(12) United States Patent
Koppes et al.

(10) Patent No.: US 7,220,328 B1
(45) Date of Patent: *May 22, 2007

(54) LOW-SMOKE GAS GENERATING LOW ORDER PRESSURE PULSE COMPOSITIONS

(75) Inventors: William M. Koppes, Adelphi, MD (US); Michael E. Sitzmann, Adelphi, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 229 days.

This patent is subject to a terminal disclaimer.

(21) Appl. No.: 10/781,955

(22) Filed: Feb. 20, 2004

Related U.S. Application Data

(63) Continuation-in-part of application No. 10/439,804, filed on May 19, 2003, now Pat. No. 6,919,453, which is a continuation-in-part of application No. 10/171,114, filed on Jun. 14, 2002, now Pat. No. 6,632,305, which is a continuation-in-part of application No. 09/874,946, filed on Jun. 6, 2001, now Pat. No. 6,423,844.

(51) Int. Cl.
*C06B 31/28* (2006.01)
*C06B 29/22* (2006.01)

(52) U.S. Cl. .......................... 149/46; 149/76

(58) Field of Classification Search ............... 149/46, 149/76, 45, 36
See application file for complete search history.

(56) References Cited

U.S. PATENT DOCUMENTS

| | | | | |
|---|---|---|---|---|
| 2,473,797 | A | 6/1949 | Kaiser et al. | 260/249.5 |
| 2,475,440 | A | 7/1949 | Walter | 260/239 |
| 3,061,605 | A | 10/1962 | D'Alelio | 260/239.7 |
| 4,549,018 | A | 10/1985 | Siedle | 544/225 |
| 4,565,815 | A | 1/1986 | Kim et al. | 514/246 |
| 6,253,680 | B1 | 7/2001 | Grubelich | 102/334 |
| 6,423,844 | B1 * | 7/2002 | Koppes et al. | 544/198 |
| 6,602,366 | B2 * | 8/2003 | Koppes et al. | 149/56 |
| 6,632,305 | B2 * | 10/2003 | Koppes et al. | 149/56 |
| 6,673,924 | B2 * | 1/2004 | Koppes et al. | 544/179 |
| 6,846,926 | B1 * | 1/2005 | Koppes et al. | 544/198 |

OTHER PUBLICATIONS

Article: "The Synthesis and Dimroth-Type Rearrangement of 5,7-Bis(dimethylamino)-3-(methylthio)-s-triazolo[4,3-a]-s-triazine", DeMilo et al., J. Heterocyclic Chem. 10, 231 (Apr. 1973), pp. 231-233.
Article: "New Synthesis of Dyes of the Triazine", Series II. VAT Dyes of the Triazolo-Triazine Series by A. Titkov and I.D. Pletnev, Scientific Research Institute of Intermediates and Dyes, translated from Zhurnal Obshchel Khimil, vol. 33, No. 4, pp. 1355-1357, Apr. 1963.
Abstract: No. 93042a Basic azo dye. Maeda, Hhigeo et al. (40-Dyes, vol. 81, 1974), referencing Maeda et al. Japan Kokai 74 24,226.
Abstract: No. 122766x Basic azo dye. Maeda, Hhigeo et al. (40-Dyes, vol. 81, 1974), referencing Maeda et al. Japan Kokai 74 27,287.
Article: "Chemistry of Dicyandiamide V Structures of Guanazo- and Pyro-Guanazoles, and Reaction of Dicyandiamide with 3-Amino-5-Substituted-1,2,4,4H-Triazoles", Kaiser et al.J. Organic Chemistry, vol. 18, 1953, pp. 1610-1614.

* cited by examiner

*Primary Examiner*—Aileen Felton
(74) *Attorney, Agent, or Firm*—Fredric J. Zimmerman

(57) ABSTRACT

Low-smoke gas generating compositions for producing a low order pressure pulse use a salt or complex of a triazolyl-tetrazinyl-triazine compound. The general chemical structure of the triazolyl-tetrazinyl-triazine is:

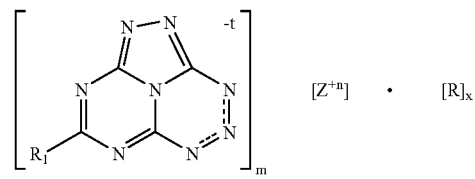

wherein $Z^+$, when present, is $H^+$ or a cation; $R_1$ is an electron donating group and wherein m=1, 2 or 3; t=0 or 1, and n=0, 1, 2 or 3; and when present, R is a complexing component and x=1, 2 or 3; wherein either Z or R may be absent.

20 Claims, No Drawings

LOW-SMOKE GAS GENERATING LOW ORDER PRESSURE PULSE COMPOSITIONS

This application is a continuation-in-part (CIP) of U.S. patent application Ser. No. 10/439,804, entitled "Colorant Compostions", filed May 19, 2003, now U.S. Pat. No. 6,919,453, which is a continuation-in-part (CIP) of U.S. patent application Ser. No. 10/171,114, entitled "1,2,4-Triazolo[4,3-a][1,3,5]Triazine-3,5,7-Substituted Precursor, and Process, and Compounds Therefrom", filed Jun. 14, 2002, now U.S. Pat. No. 6,632,305, issued Oct. 12, 2003, which is a continuation-in-part (CIP) of U.S. patent application Ser. No. 09/874,946, entitled "Process for Making 1,2,4-Triazolo [4,3-a][1,3,5]Triazine-3,5,7-Triamine", filed Jun. 6, 2001, now U.S. Pat. No. 6,423,844, issued Jul. 23, 2002.

STATEMENT OF GOVERNMENT INTEREST

The invention described herein may be manufactured and used by or for the Government of the United States of America for governmental purposes without payment of any royalties thereon or therefor.

BACKGROUND OF THE INVENTION

1. Field of the Invention

The present invention pertains to novel high nitrogen content, low carbon content energetic compounds. More particularly, the present invention pertains to triazolyl-tetrazinyl-triazine compounds, and complexes and salts thereof. The triazolyl-tetrazinyl-triazine compounds, and their complexes and salts, of the present invention are particularly useful as energetic ingredients in low-smoke gas generating compositions, most particularly for producing a low order pressure pulse.

2. Brief Description of the Related Art

Stun grenades, and similar flash-bang devices, are used by the military and law enforcement personnel to incapacitate or confuse an adversary, such as a terrorist, criminal suspect or enemy soldier, to facilitate their apprehension or to free a hostage. When used, these diversionary devices emit a blaring noise usually accompanied by a temporarily blinding flash of light, and are generally most effective in a confined space such as a room. The use of the stun grenade temporarily distracts anyone in the space for a limited time that is sufficient to enable safe entry into the space and overpower the adversary.

Stun grenades should be designed in a manner which causes minimal or no permanent damage to the persons against whom the grenades are used. The devices generally have a short time delay fuse and an explosive charge. The devices are thrown into the room containing the suspects just prior to the assault. The "stun" or disorienting effect comes from the loud explosion and the blinding effect from the flash which accompanies the explosion. Additionally, the explosive within the stun grenade, while maximizing the amount of flash and noise, should impart a minimum amount of smoke to ensure the safe entry into the space. Devices that produce large volumes of smoke significantly hinder actions of an entry team. If the entry team waits for the smoke to clear, the stun effect has worn off, negating the advantage of using the device.

There is a need in the art to provide a low-smoke gas generating composition for producing a low order pressure pulse. The present invention addresses this and other needs.

SUMMARY OF THE INVENTION

The present invention includes a low-smoke gas generating composition for producing a low order pressure pulse comprising a compound having the chemical structure:

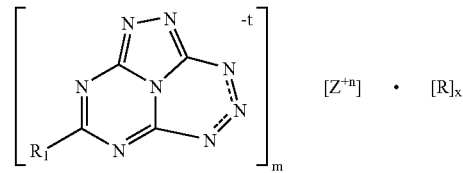

wherein, when present, $Z^+$ is $H^+$ or a cation; $R_1$ is an electron donating group and wherein m=1, 2 or 3; t=0 or 1, and n=0, 1, 2 or 3; and when present, R is a complexing component and x=1, 2 or 3; wherein either Z or R may be absent.

DETAILED DESCRIPTION OF THE INVENTION

The present invention includes novel triazolyl-tetrazinyl-triazine compounds, particularly triazolyl-tetrazinyl-aminotriazine compounds, and the complexes and salts thereof, that are particularly useful in low-smoke gas generating compositions (also referred to herein as "low-smoke compositions") while producing low order pressure pulse. Preferably the low-smoke compositions of the present invention are characterized as essentially smoke-free. Low-smoke compositions have limited amounts of residual smoke after burn. The triazolyl-tetrazinyl-triazine compounds, and their complexes and salts, of the present invention provide a high-nitrogen content, low-carbon content energetic material as a principal component within the low-smoke composition. Low-smoke compositions of the present invention include those compositions where a minimal amount of excess carbon and hydrogen remain after initiation of the explosive. As such, the amount of smoke residing in a space immediately after initiation of the explosive does not obscure objects within a confined space, such as a room having 2000 cubic feet of space. This allows an entry team to access the confined space immediately after deflagration of the explosive. For example, U.S. Pat. No. 6,253,680, to Grubelich, entitled "Diversionary Device", the disclosure of which is herein incorporated by reference, describes functional aspects of such devices.

The term low order pressure pulse include pressure pulses that are not expected to kill or maim a person in the normal course of use of the explosive as a stunning device. Typically, ranges between the exploding device and person are from about six inches to about ten feet, with ranges of from about five feet to about eight feet more common. As such, low-smoke compositions of the present invention are generally configured to react as a low explosive, i.e., non-detonating, that deflagrates. Through deflagration, very rapid autocombustion of explosive particles occurs as a surface phenomenon.

The low-smoke gas generating compositions of the present invention include a compound having the chemical structure:

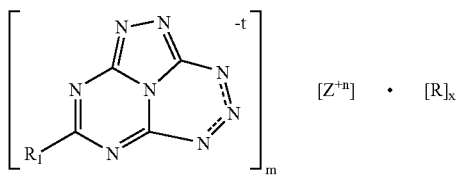

wherein, when present, $Z^+$ is $H^+$ or a cation; $R_1$ is an electron donating group and wherein m=1, 2 or 3; t=0 or 1, and n=0, 1, 2 or 3; and when present, R is a complexing component and x=1, 2 or 3; wherein either Z or R may be absent.

Substituent $R_1$ is an electron donating group. Preferred electron donating groups include $-OCH_3$, $-NH_2$, $-NHNH_2$, $-N_3$, and the like, including combinations of different electron donating groups.

In one embodiment $Z^+$ comprises $H^+$. When $Z^+$ is present as a cation, a salt is formed. Cations of the present invention include those molecules effective for low-smoke gas generating compositions. As such, cations of the present invention generally increase the amount of nitrogen in the composition, while maintaining a minimal amount of carbon present. The triazolyl-tetrazinyl-triazine compounds also provide a platform for a very large number of specialized salts useful in the low-smoke field, including those of amines or other cations. Preferred compounds include amine salts, and more preferably include $Z^+$ such as $H_2NC(NH_2)NHCONH_2$, $C(NHNH_2)_3$, $NH_2NH_3$, $NH_4$, $H_2NNHC(NH_2)NH_2$, $(H_2NNH)_2C(NH_2)$, $H_2NNH(C_2N_4)NHNH_3$, $C(NH_2)_3$, $(HONH_3)$, and bis(1(2)H-tetrazol-5-yl)-amine$(C_2H_4N_9)$, the monohydrate of bis(1(2)H-tetrazol-5-yl)-amine $(C_2H_4N_9H_2O)$.

In another embodiment, the presence of R forms a complex. The R component of the present invention includes appropriate complexing molecules effective for low-smoke gas generating compositions. Preferably R comprises an amine complex, which increases the amount of nitrogen in the composition, while maintaining a minimal amount of carbon present. The complex form of the triazolyl-tetrazinyl-triazine occurs when $Z^+$ comprises $H^+$, and the value of x is not 0. The complex form includes the hydrogen attached to a nitrogen atom in the tetrazinyl ring (see e.g. Example 11B). Complexes of the present invention include, for example, R=Dihydrazino-s-tetrazine, Trihydrazino-s-triazine, 5-Aminotetrazole, N-aminotriazoles, and bis-(1(2)H-tetrazol-5-yl)-amine.

The low-smoke compositions herein preferably include non-metal triazolyl-tetrazinyl-aminotriazine compound salts. In one particular embodiment, preferably m=n.

In addition to a complex or salt structure of the triazolyl-tetrazinyl-triazine compound, a useful structure of the present invention includes a low-smoke triazolyl-tetrazinyl-triazine compound having a triazolyl-tetrazinyl-aminotriazine structure that includes $Z^+$ being $H^+$, t=1, m=1, n=1, and x=0. When $Z^+$ comprises $H^+$, and m and n are both equal to 1, the calculated heat of formation is approximately 255 kcal/mole (gas phase), and a density of approximately 1.77 g/cc (calcd) which provides significant energy to the low-smoke composition.

Additionally, the low-smoke gas generating composition of the present invention may include an oxidant. Preferred oxidants include ammonium perchlorate, ammonium nitrate, and combinations thereof. The low-smoke composition generally includes the addition of an oxidant to fully consume the carbon and hydrogen components of the low-smoke compositions during burning. Suitable oxidizers can generally include, without limitation, one or more alkaline earth metal nitrates, alkaline earth metal nitrites, alkali metal nitrates, alkali metal nitrites, transition metal oxides, such as ammonium perchlorate, alkali perchlorates such as potassium perchlorate and the like, ammonium nitrate, and alkali nitrates such as potassium nitrate and the like, or combinations thereof. Examples of the oxidizer include at least one of an alkali metal or an alkaline earth metal nitrate, a complex salt nitrate, such as $Ce(NH_4)_2(NO_3)_6$ or $ZrO(NO_3)_2$, a dried, hydrated nitrate, such as $Ca(NO_3)_2.4H_2O$ or $Cu(NO_3)_2.2.5\ H_2O$, silver nitrate, an alkali or alkaline earth metal chlorate or perchlorate, ammonium perchlorate, a nitrite of sodium, potassium, or silver. Additionally, organic compositions such as a solid organic nitrate, nitrite, or amine, such as guanidine nitrate, nitroguanidine and 5-aminotetrazole may be included. The oxidizer may include silver nitrate or a co-melt or mixture comprising silver nitrate and at least one of an alkali metal nitrate, an alkaline earth metal nitrate, a complex salt nitrate, a dried, hydrated nitrate, an alkali metal chlorate, an alkali metal perchlorate, an alkaline earth metal chlorate, an alkaline earth metal perchlorate, ammonium perchlorate, sodium nitrite, potassium nitrite, silver nitrite, or a complex salt nitrite; and independently a solid organic nitrate, a solid organic nitrite, or a solid organic amine. Alkali chlorates are generally not preferred as oxidizer due to sensitivity concerns. Ammonium perchlorate and ammonium nitrate are preferred oxidizers as the absence of any metal ions eliminates any ash residue. Ammonium nitrate is hygroscopic and compositions including ammonium nitrate must be protected from moisture. The oxidizer is generally added with the triazolyl-tetrazinyl-triazine compounds, or their complexes or salts, in amounts sufficient to provide about three equivalents of free oxygen. For example, the ammonium perchlorate oxidizes the triazolyl-tetrazinyl-aminotriazine anion to carbon dioxide and water if in a ratio of two parts by weight ammonium perchlorate to one part of the organic anion. The same degree of oxidation requires four parts ammonium nitrate. Generally, the compositions can include from about 30 percent by weight to about 60 percent by weight of the high-nitrogen content, low-carbon content energetic material, more preferably from about 35 percent by weight to about 55 percent by weight, together with about 40 to about 60 percent by weight of the selected oxidizer. One preferred low-smoke formulation includes a triazolyl-tetrazinyl-aminotriazine compound together with two parts ammonium perchlorate as the oxidizer for complete oxidation.

The low-smoke composition is formed from mixing or packing the triazolyl-tetrazinyl-triazine compound, including its salt or complex, in an appropriate delivery combination for use as a stunning device, with the appropriate mixing and packing being within the capabilities of a person of ordinary skill in the art of manufacturing stunning devices. The triazolyl-tetrazinyl-aminotriazine compound is prepared by diazotization of the triazolyl-triaminotriazine precursor, as taught herein, to form the appropriate low-smoke salt. Diazotization occurs by reacting the triazolyl-triaminotriazine precursor with a nitrite salt, such as, without limitation, nitric oxide, sodium nitrite, potassium nitrite and the like. The triazolyl-triaminotriazine precursor(s), including the acid salts thereof, are diazotized in an appropriate aqueous acid, such as for example hydrochloric or sulfuric acid, with the nitrite salt to give the ring-closed tetrazine product of the triazolyl-tetrazinyl-triazine compound, preferably a triazolyl-tetrazinyl-triazine compound. The use of sodium nitrite (Z=Na) to form the triazolyl-tetrazinyl-aminotriazine compound is preferred. The triazolyl-tetrazinyl-aminotriazine compound (Z=Na) can be acidified to produce the parent acid of the triazolyl-tetrazinyl-aminotriazine compound (i.e., Z=H). Other triazolyl-tetrazinyl-aminotriazine compounds may be formed by neutralization of the parent acid or by cation exchange reactions with the sodium salt.

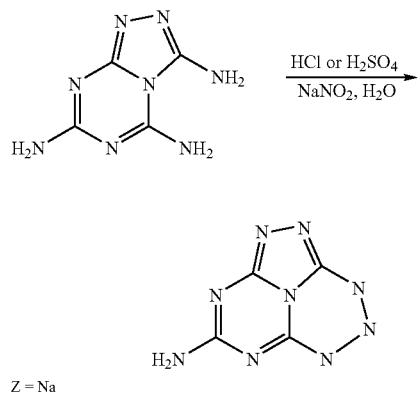

The preparation of triazolyl-tetrazinyl-aminotriazine salts by neutralization of the parent acid (Method A) occurs by reaction with amine bases or by reaction with metal hydroxides. Cation exchange with the sodium salt to form the triazolyl-tetrazinyl-aminotriazine salts (Method B) occurs by the process that includes an aqueous solution of the sodium salt being mixed with an amine salt, such as triaminoguanidinium nitrate, triaminoguanidinium chloride, diaminoguanidinium hydrochloride, guanidinium hydrochloride, etc.

Precursor

The precursor comprises a 1,2,4-triazolo[4,3-a][1,3,5]triazine-3,5,7-triamine, acid salt or its neutralized form of 1,2,4-triazolo[4,3-a][1,3,5]triazine-3,5,7-triamine. The general process involves ring closure of 2,4-diamino-6-hydrazino-s-triazine with an acid and a chemical of the general formula RCN where the R comprises a leaving group, and then neutralizing the acid salt crystals. It is preferred to use the acid salt crystal directly in the diazotization step without prior neutralization.

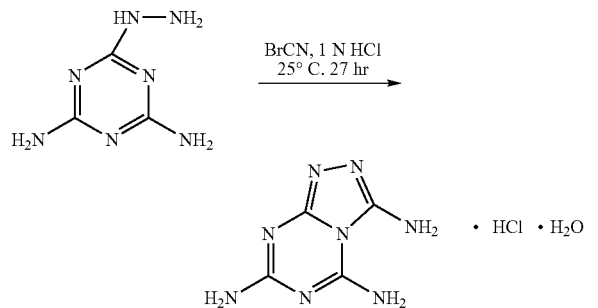

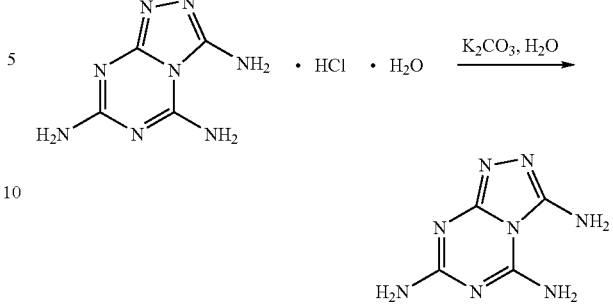

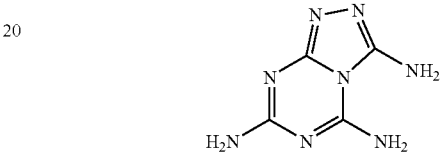

The structure of the precursor is shown below:

More specifically, the 1,2,4-triazolo[4,3-a][1,3,5]triazine-3,5,7-triamine, acid salt is derived first by obtaining or synthesizing 2,4-diamino-6-hydrazino-s-triazine. One method for synthesizing this chemical is set forth in U.S. Pat. No. 3,061,605 by D'Alelio. The general method is to effect a reaction between 2,4-diamino-6-chloro-1,3,5-triazine and hydrazine. A specific example is set forth in column 3, lines 60–70 of the above patent which is hereby incorporated by reference. While this particular method of synthesizing 2,4-diamino-6-hydrazino-s-triazine is specifically disclosed, any prior art method of synthesis would be appropriate to practice the present invention. The 2,4-diamino-6-hydrazino-s-triazine is dissolved with an acid, preferably at room temperature with an acid that is of sufficient strength to dissolve the 2,4-diamino-6-hydrazino-s-triazine. Many acids can be employed in the present invention, such as sulfuric acid or hydrochloric acid or mixtures of these acids with other solvents such as methanol or ethanol, and may be selected by one skilled in the art. One preferred acid is 1N hydrochloric acid. The dissolved 2,4-diamino-6-hydrazino-s-triazine is mixed with a reagent of the formula RCN, wherein R comprises a leaving group. This reaction will provide the amino triazole ring on the product directly. A leaving group, as used in this application, is a group that can be displaced to give ring closure; that is, produces the amino triazole ring. One preferred leaving group comprises bromine wherein the reagent comprises cyanogen bromide. Although the reaction in this step is acid catalyzed, preferred reaction times range from about twenty hours to about thirty hours in order to allow for the maximum formation of acid salt crystals. It is also preferred that the acid salt crystals be removed after the reaction is substantially complete, approximately thirty hours, to prohibit contamination of the final product with impurities. The crystals may be removed by any normal method, such as filtration, and can then be washed and dried in order to obtain the final acid salt product.

Neutralization of the 1,2,4-triazolo[4,3-a][1,3,5]triazine-3,5,7-triamine, acid salt crystals synthesized above to obtain a final product of 1,2,4-triazolo[4,3-a][1,3,5]triazine-3,5,7-triamine is accomplished by mixing the crystals with a substance more basic than 1,2,4-triazolo[4,3-a][1,3,5]triazine-3,5,7-triamine. This step results in the removal of the acid from the acid salt crystals and provides for a final product of 1,2,4-triazolo[4,3-a][1,3,5]triazine-3,5,7-triamine. The substance used in this final step may be selected by one skilled in the art based upon the basicity of the substance versus the basicity of 1,2,4-triazolo[4,3-a][1,3,5] triazine-3,5,7-triamine. Some examples are potassium carbonate, potassium acetate, sodium bicarbonate, and sodium hydroxide. One preferred substance is potassium carbonate. It is also preferred that the reaction take place in solution, so preferably, water or some other solvent may be added to the salt.

The following examples (Examples 1A–1C) are preparations of the 1,2,4-triazolo[4,3-a][1,3,5]triazine-3,5,7-triamine precursors:

EXAMPLE 1A

Preparation of 1,2,4-triazolo[4,3-a][1,3,5]triazine-3, 5,7-triamine, Hydrochloric Salt Hydrate To 126 g of 1 N hydrochloric acid stirred at 25° C. was added 9.06 g (0.0570 mole) of 2,4-diamino-6-hydrazino-s-triazine [prepared according to G. F. D'alelio, U.S. Pat. No. 3,061,605 (1962), which is incorporated herein by reference]. The mixture was stirred for 10 minutes, at which time nearly all of the 2,4-diamino-6-hydrazino-s-triazine had dissolved. Cyanogen bromide (9.3 g, 0.0877 mole) was added at one time and, after 5 minutes, all of the material was in solution. After about 1 hour, crystals began to precipitate. After 3 hours, stirring was stopped and the mixture was allowed to stand for an additional 24 hours to continue precipitation of crystals. The crystals were removed by filtration and washed with 2×25 ml cold water. The crystals were air dried and then dried in a vacuum desiccator over Drierite to give 8.60 g (68.4% yield) of product. IR (KBr): 3300, 3155, 1708, 1695, 1624, 1534, 1490, 1444, 1339, 1173, 1073, 979, 845, 772 cm$^{-1}$. Anal. Calcd for $C_4H_6N_8$ (HCl) ($H_2O$): C, 21.77; H, 4.11; N, 50.79; Cl, 16.07. Found: C, 21.84; H, 4.25; N, 50.02; Cl, 16.02.

EXAMPLE 1B

Preparation of 1,2,4-triazolo[4,3-a][1,3,5]triazine-3,5,7-triamine: To 6.86 g (0.031 mole) of 1,2,4-triazolo[4,3-a][1,3,5]triazine-3,5,7-triamine, hydrochloric salt hydrate stirred in 175 ml of water was added 4.40 g (0.031 mole) of potassium carbonate and the mixture was stirred vigorously for 40 minutes. The solid was removed by filtration, washed with water, and dried to give 4.83 g (94%) of 1,2,4-triazolo[4,3-a][1,3,5]triazine-3,5,7-triamine. $^{13}$C NMR ($CD_3CO_2D/D_2O$, 1:1 by vol): 145.7, 151.1, 151.9, 164.0. $^{13}$C NMR ($D_2SO_4$): 133.6, 141.9, 143.1, 149.5. IR (KBr): 3413, 3314, 3096, 1654, 1611, 1540, 1480, 1430, 1375, 979, 859, 770 cm$^{-1}$. Anal. Calcd for $C_4H_6N_8$: C, 28.92; H, 3.64; N, 67.44. Found: C, 28.64; H, 3.65; N, 66.08.

EXAMPLE 1C

Preparation of 1,2,4-triazolo[4,3-a][1,3,5]triazine-3, 5,7-triamine, Hydrochloric Salt Hydrate To 0.31 g (0.003 mole) of 37% hydrochloric acid in water (4 ml) and methanol (21 ml) stirred at 25° C. was added 0.42 g (0.003 mole) of 2,4-diamino-6-hydrazino-s-triazine [prepared according to G. F. D'alelio, U.S. Pat. No. 3,061,605 (1962)]. Cyanogen bromide (0.32 g, 0.003 mole) was then added at one time. The solution was held at 77–80° C. for 3 hours, before it was cooled to 25° C. and a small amount of solid was removed by filtration. The volatiles were removed from the filtrate to give 0.60 g of solid that was mainly 1,2,4-triazolo[4,3-a][1,3,5]triazine-3,5,7-triamine, hydrochloric salt hydrate by TLC and IR analyses.

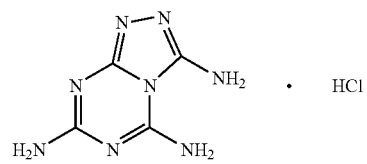

Examples 1A and 1C

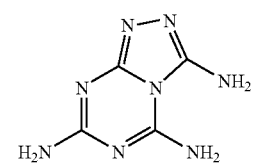

Example 1B

EXAMPLE 1D

Preparation of triazolyl-tetrazinyl-aminotriazine, Sodium Salt (Z═Na)

Sodium nitrite (18.0 g, 0.26 mole) was added to a stirred mixture of 9.0 g (0.0408 mole) of 1,2,4-triazolo[4,3-a][1,3,5]triazine-3,5,7-triamine, hydrochloric salt hydrate in 265 mL of water. The flask was stoppered and the mixture was stirred vigorously at 23–24° C. for 3 hours and 20 minutes. The orange-colored mixture was heated to 70° C. over 15–20 minutes and was held at 70° C. for one hour before the hot mixture was filtered to remove a finely divided insoluble brown solid. The insoluble solid was washed with 5×15 mL of hot water (60° C.) until the washings were light red in color. The filtrate was refrigerated at 5° C. overnight to give a precipitate of red crystals that were removed by filtration and washed with 2×15 mL of ice water to yield 6.81 g of triazolyl-tetrazinyl-aminotriazine, sodium salt hydrate. An additional 1.05 g was obtained by concentration of the filtrate under reduced pressure to bring the total yield to 7.86 g (89%).

EXAMPLE 1E

Preparation of triazolyl-tetrazinyl-aminotriazine, Sodium Salt (Z═Na)

1,2,4-triazolo[4,3-a][1,3,5]triazine-3,5,7-triamine, hydrochloric acid salt hydrate (4.20 g, 0.0190 mole) was added to aqueous hydrochloric acid stirred in an ice bath to produce a slurry [The aqueous hydrochloric acid was prepared by adding 8.0 g of 37% concentrated HCl (0.08 mole HCl) to 75 ml of water]. The ice-cold slurry was added in seven portions over approximately 15 minutes to a solution of 16.5 g (0.24 mole) of sodium nitrite in 50 ml of water stirred in an ice bath. Stirring in the ice bath was continued for two hours before the yellow mixture was allowed to warm to 20° C. over approximately one hour. The mixture was heated to 60° C. over 30 minutes and then held at 60–65° C. for one hour. The hot mixture was filtered to remove an insoluble brown solid, after which the filtrate was cooled to 5° C. to give 2.16 g of red crystals. Concentration of the aqueous mother liquor under reduced pressure gave an additional 0.73 g of product to bring the total yield to 2.89 g (70%), mp>300.degree. C. (gradual decomp. with loss of red color above 220° C.). The product contains a small amount of a by-product (nitrotriazolo-diaminotriazine) which can be removed by filtration when the product is dissolved in warm water. Analysis showed: $^1$H NMR (DMSO-$d_6$): 6.67 (s). $^{13}$C NMR (DMSO-$d_6$): 146.1, 151.7, 153.1, 167.7. Anal. Calcd for $C_4H_2N_9$ Na(H$_2$O): C, 22.13; H, 1.86; N, 58.06, Na, 10.59. Found: C, 22.04; H, 1.93; N, 57.35, Na, 11.00.

EXAMPLE 1F

Preparation of triazolyl-tetrazinyl-aminotriazine, Sodium Salt (from Triazolo-triaminotriazole)

An ice cold slurry of 0.63 g (0.0038 mole) of 1,2,4-triazolo[4,3-a][1,3,5]triazine-3,5,7-triamine in 15 ml of aqueous sulfuric acid (containing 1.0 g, 0.01 mole H$_2$SO$_4$) was added in 1.5 ml portions over 5 minutes to a solution of 3.3 g (0.048 mole) of sodium nitrite in 10 ml of water stirred in an ice bath. The mixture was stirred at ice bath temperature for 2.5 hours before it was held at 20° C. for 10 minutes and then at 50–53° C. for 45 minutes. The warm mixture was filtered to remove an insoluble brown solid and the filtrate was held at 80–85° C. for 15 minutes. The red solution was allowed to stand at room temperature to precipitate red crystals (0.33 g). Concentration of the mother liquor gave additional product, raising the total to 0.43 g (52%).

The following examples (Examples 2–11) are preparations of the triazolyl-tetrazinyl-triazine compounds of the present invention with corresponding structures that exemplify non-limiting examples of possible salts for use in the low-smoke compositions of the present invention:

EXAMPLE 2

Preparation of triazolyl-tetrazinyl-aminotriazine, (Parent Acid) (Z=H)

Triazolyl-tetrazinyl-aminotriazine, sodium salt hydrate (2.9 g, 0.0134 mole) was dissolved in 70 ml of warm water. The solution was stirred at 25° C. while adding dropwise 15 ml of 1N aqueous hydrochloric acid. The yellow precipitate that formed was removed by filtration and washed with cold water to give 1.9 g (81%) of yellow solid, mp 215° C., rapid decomposition. Analysis showed: $^1$H NMR (DMSO-$d_6$): 13.65 (very broad signal, 1H), 8.06, 7.96 (d, 2H). $^{13}$C NMR (DMSO-$d_6$): 143.9 (1C), 149.6 (2C), 167.5 (1C).

Examples 3 through 11 describe the preparation of additional salts of triazolyl-tetrazinyl-aminotriazine either by neutralization of the parent acid (Method A) or by cation exchange with the sodium salt (Method B).

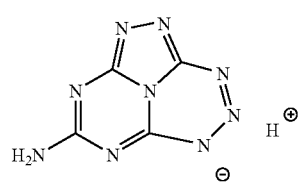

Example 2

EXAMPLE 3

Preparation of triazolyl-tetrazinyl-aminotriazine, Guanyl Urea Salt (Z=H$_2$NC(NH$_2$)NHCONH$_2$) Via Neutralization of the Parent Acid (Method A)

A solution of 0.15 g (0.5 mmole) of N-guanyl urea sulfate hydrate, [H$_2$NC(NH$_2$)NHCONH$_2$]$_2$ H$_2$SO$_4$ xH$_2$O, in 3 ml of water was neutralized with 1 ml of aqueous sodium hydroxide (containing 0.04 g, 1 mmole of NaOH). This solution (containing N-guanyl urea as a free base) was added dropwise to a stirred suspension of the parent acid (triazolo-tetrazino-aminotriazine) in 3 ml of water. The mixture was stirred for 2 hours at 25° C., then was cooled to 5° C., and the insoluble product was removed by filtration and washed with cold water to give 0.24 g (96%) of red solid, mp>300° C. (gradual decomp. with loss of red color above 240° C.). Analysis showed: $^1$H NMR (DMSO-$d_6$): 6.73 (s, 2H) 7.09 (broad signal, 2H), 8.04 (very broad signal, 4H). $^{13}$C NMR (DMSO-$d_6$): 146.1, 151.7, 153.1, 154.6, 155.2, 167.7. Anal. Calcd for $C_6H_9N_{13}O$ (H$_2$O): C, 24.24; H, 3.73; N, 61.26. Found: C, 24.19; H, 3.68; N, 60.71. X-ray crystal structure analysis also confirmed the structure of the product to be triazolyl-tetrazinyl-aminotriazine, guanyl urea salt hydrate.

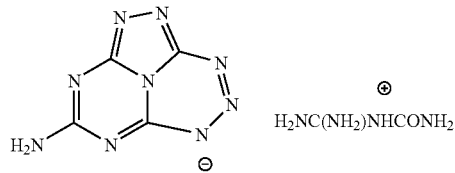

Example 3

EXAMPLE 4

Preparation of triazolyl-tetrazinyl-aminotriazine, Triaminoguanidine Salt [Z=C(NHNH$_2$)$_3$] Via Cation Exchange (Method B)

A solution of triazolyl-tetrazinyl-aminotriazine, sodium salt hydrate (0.32 g, 1.45 mmole) in 10 ml of water was stirred at 25° C. while triaminoguanidinium nitrate (0.25 g, 1.50 mmole) was added in three portions over one minute. After a short time, red crystals began to precipitate from the solution. The mixture was stirred at 25° C. for two hours before it was cooled to 5° C. and filtered to give 0.25 g of red crystals. Additional product from concentration of the filtrate raised the total yield to 0.29 g (71%), mp 195° C., rapid dec. Recrystallization from water raised the mp to 203° C., rapid dec. Analysis showed: $^1$H NMR (DMSO-$d_6$): 4.48 (s, 6H), 6.65 (s, 2H), 8.59 (s, 3H). $^{13}$C NMR (DMSO-$d_6$): 146.1, 151.7, 153.1, 158.9, 167.7. Anal. Calcd for $C_5H_{11}N_{15}$ (H$_2$O): C, 20.07; H, 4.38; N, 70.21. Found: C, 20.22; H, 4.30; N, 69.64.

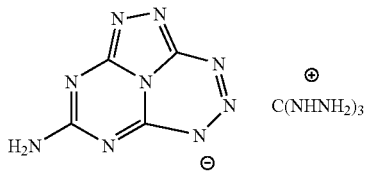

Example 4

EXAMPLE 5

Preparation of triazolyl-tetrazinyl-aminotriazine, Hydrazinium Salt [Z=NH$_2$NH$_3$]

Via Method A: The parent acid was neutralized with one equivalent of aqueous hydrazine to give red crystals (74%), mp 200° C., rapid dec. Analysis showed: $^1$H NMR (DMSO-d$_6$): 6.68 (s) (merged with abroad s at 7.05). $^{13}$C NMR (DMSO-d$_6$): 146.1, 151.7, 153.1, 167.7. Anal. Calcd for C$_4$H$_7$N$_{11}$: C, 22.96; H, 3.38; N, 73.66. Found: C, 23.06; H, 3.51; N, 71.56.

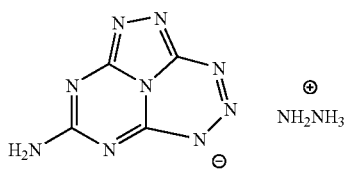

Example 5

EXAMPLE 6

Preparation of triazolyl-tetrazinyl-aminotriazine, Ammonium Salt [Z=NH$_4$]

Via Method A: The parent acid was neutralized in water with one equivalent of aqueous ammonia to give red crystals (74%), mp>300° C. (with gradual decomp and loss of red color above 220° C.). Analysis showed: $^1$H NMR (DMSO-d$_6$): 6.69 (s) 7.12 (bs). $^{13}$C NMR (DMSO-d$_6$): 146.1, 151.7, 153.1, 167.7. Anal. Calcd for C$_4$H$_6$N$_{10}$: C, 24.74; H, 3.12; N, 72.14. Found: C, 24.40; H, 3.04; N, 70.23.

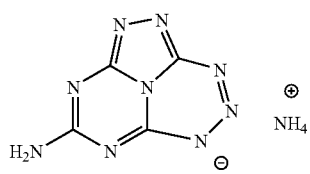

Example 6

EXAMPLE 7

Preparation of triazolyl-tetrazinyl-aminotriazine, Aminoguanidinium Salt [Z=H$_2$NNHC(NH$_2$)NH$_2$]

Via Method A: The parent acid was neutralized in water with aminoguanidine bicarbonate [H$_2$NNHC(=NH)NH$_2$ (H$_2$CO$_3$)] using equal molar amounts to give red crystals (81%), mp 227° C., dec. Analysis showed: $^1$H NMR (DMSO-d$_6$): 4.68 (s, 2H), 6.67 (s, 2H), 6.76, 7.23 (two bs, 4H), 8.58 (s, 1H). $^{13}$C NMR (DMSO-d$_6$): 146.1, 151.7, 153.1, 158.5, 167.7. Anal. Calcd for C$_5$H$_9$N$_{13}$: C, 23.90; H, 3.61; N, 72.48. Found: C, 23.65; H, 3.65; N, 70.91.

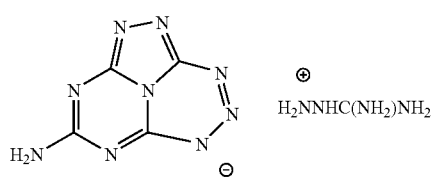

Example 7

EXAMPLE 8

Preparation of triazolyl-tetrazinyl-aminotriazine, Diaminoguanidinium Salt [Z=(H$_2$NNH)$_2$C(NH$_2$)]

Via Method B: The sodium salt hydrate and diaminoguanidinium hydrochloride were combined in equimolar amounts in water to give a precipitate of red crystals (71%), mp 196° C., dec. Recrystallization from water gave mp 199° C., dec. Analysis showed: $^1$H NMR (DMSO-d$_6$): 4.59 (s, 4H), 6.68 (s, 2H), 7.16 (s, 2H), 8.58 (s, 2H). $^{13}$C NMR (DMSO-d$_6$): 146.1, 151.7, 153.1, 159.7, 167.7. Anal. Calcd for C$_5$H$_{10}$N$_{14}$: C, 22.56; H, 3.79; N, 73.66. Found: C, 22.52; H, 3.89; N, 71.88.

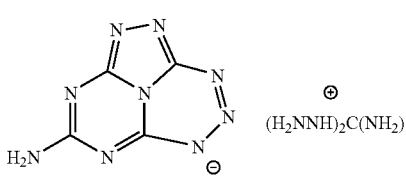

Example 8

EXAMPLE 9

Preparation of triazolyl-tetrazinyl-aminotriazine, Guanidinium Salt [Z=C(NH$_2$)$_3$]

Via Method B: The sodium salt hydrate and guanidinium hydrochloride were combined in equimolar amounts in water to give a precipitate of red crystals (73%), mp 263° C., dec. Analysis showed: $^1$H NMR (DMSO-d$_6$): 6.69 (s, 2H), 6.95(s, 6H). $^{13}$C NMR (DMSO-d$_6$): 146.1, 151.7, 153.1, 157.6, 167.7. Anal. Calcd for C$_5$H$_8$N$_{12}$ (H$_2$O): C, 23.62; H, 3.96; N, 66.12. Found: C, 23.53; H, 3.96; N, 64.12.

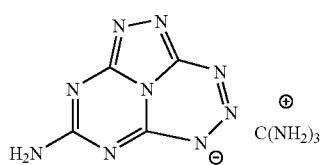

Example 9

EXAMPLE 10

Preparation of triazolyl-tetrazinyl-aminotriazine, Triethylamine Salt [Z=HN(C$_2$H$_5$)$_3$]

Via Method A: The parent acid was treated with an equimolar amount of triethylamine in methanol. The solvent was partially removed under reduced pressure to give red crystals, mp 205° C., dec. The product is the triethylamine salt, which has separated from solution in the form of a complex with an additional molecule of the parent acid. Analysis showed: $^1$H NMR (DMSO-d$_6$): 1.17 (t, 9H), 3.10 (q, 6H), 3.82 (very broad s), 7.33 (broad s, 3H). $^{13}$C NMR (DMSO-d$_6$): 8.4, 45.6, 145.1, 150.7, 151.4, 167.6. Anal. Calcd for C$_{10}$H$_{18}$N$_{10}$ (C$_4$H$_3$N$_9$): C, 36.92; H, 4.65; N, 58.43. Found: C, 36.54; H, 4.73; N, 57.56.

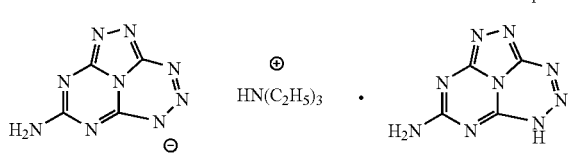

Example 10

EXAMPLE 11

Preparation of triazolo-tetrazino-aminotriazine, 3,6-dihydrazino-1,2,4,5-tetrazine Salt [Z=H$_2$NNH(C$_2$N$_4$)NHNH$_3$]

Via Method A: The parent acid was stirred in methanol/water with an equimolar amount of 3,6-dihydrazino-1,2,4,5-tetrazine (DHT) for 5 hours. The mixture was filtered to remove the rust colored solid, mp 165° C., very rapid dec. [For comparison, the dec. points of DHT and the parent acid are 155° C. and 215° C., respectively]. $^1$H NMR (DMSO-d$_6$): 3.0–7.0 (various broad absorptions), 7.76, 7.69 (d), 8.52 (s). $^{13}$C NMR (DMSO-d$_6$): 144.4, 149.7, 150.6 (broadened), 162.4, 163.2, 167.7. For comparison spectra, DHT shows $^1$H NMR (DMSO-d$_6$): 4.25 (s, 4H), 8.38 (s, 2H)) and $^{13}$C NMR (DMSO-d$_6$): 163.3. The NMR spectra of the parent acid are given in example 2 above.

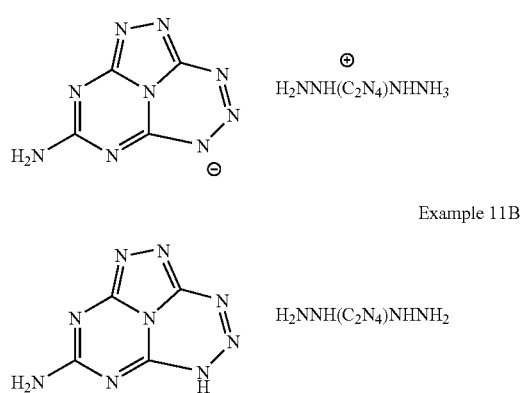

Example 11A

Example 11B

The triazolyl-tetrazinyl-triazine compounds of the low-smoke compositions of the present invention are high-nitrogen heterocyclic compounds that are particularly useful energetic ingredients in explosive devices such as stun or flash grenades and similar devices because of their thermal stability, insensitivity, and their capability to moderate flame temperatures and propellant burn rates.

The foregoing summary, description, and examples of the invention are not intended to be limiting, but are only exemplary of the inventive features which are defined in the claims.

What is claimed is:

1. A low-smoke gas generating composition for producing a low order pressure pulse comprising a compound having the chemical structure:

$$\left[\begin{array}{c}\text{structure}\\R_1\end{array}\right]_m \quad [Z^{+n}] \quad ! \quad [R]_x$$

wherein $Z^+$, when present, is $H^+$ or a cation; $R_1$ is an electron donating group and wherein m=1, 2 or 3; t=0 or 1, and n=0, 1, 2 or 3; and when present, R is a complexing component and x=1, 2 or 3; wherein either Z or R may be absent.

2. The low-smoke gas generating composition of claim 1, wherein $Z^+$ is $H^+$.

3. The low-smoke gas generating composition of claim 1, wherein $Z^+$ is a cation.

4. The low-smoke gas generating composition of claim 1, wherein $R_1$ is selected from the group consisting of —OCH$_3$, —NH$_2$, —NHNH$_2$, —N$_3$ and combinations thereof.

5. The low-smoke gas generating composition of claim 4, wherein $R_1$ is selected from the group consisting of —OCH$_3$, —NH$_2$ and combinations thereof.

6. The low-smoke gas generating composition of claim 4, wherein $R_1$ is selected from the group consisting of —NHNH$_2$, —N$_3$ and combinations thereof.

7. The low-smoke gas generating composition of claim 1, wherein Z comprises an amine.

8. The low-smoke gas generating composition of claim 1, wherein $Z^+$ is selected from the group consisting of H$_2$NC(NH$_2$)NHCONH$_2$, C(NHNH$_2$)$_3$, NH$_2$NH$_3$, NH$_4$, H$_2$NNHC(NH$_2$)NH$_2$, (H$_2$NNH)$_2$C(NH$_2$), H$_2$NNH(C$_2$N$_4$)NHNH$_3$ and C(NH$_2$)$_3$.

9. The low-smoke gas generating composition of claim 8, wherein $Z^+$ is H$_2$NC(NH$_2$)NHCONH$_2$.

10. The low-smoke gas generating composition of claim 8, wherein $Z^+$ is C(NHNH$_2$)$_3$.

11. The low-smoke gas generating composition of claim 8, wherein $Z^+$ is NH$_2$NH$_3$.

12. The low-smoke gas generating composition of claim 8, wherein $Z^+$ is NH$_4$.

13. The low-smoke gas generating composition of claim 8, wherein $Z^+$ is H$_2$NNHC(NH$_2$)NH$_2$.

14. The low-smoke gas generating composition of claim 8, wherein $Z^+$ is (H$_2$NNH)$_2$C(NH$_2$).

15. The low-smoke gas generating composition of claim 8, wherein $Z^+$ is H$_2$NNH(C$_2$N$_4$)NHNH$_3$.

16. The low-smoke gas generating composition of claim 8, wherein $Z^+$ is C(NH$_2$)$_3$.

17. The low-smoke gas generating composition of claim 1, further comprising an oxidant.

18. The low-smoke gas generating composition of claim 17, wherein the oxidant is selected from the group consisting of ammonium perchlorate, ammonium nitrate, and combinations thereof.

19. An explosive device comprising the low order explosive of claim 1.

20. A stun grenade comprising the low order explosive of claim 1.

* * * * *